United States Patent [19]

Dam et al.

[11] Patent Number: 5,119,316

[45] Date of Patent: Jun. 2, 1992

[54] METHOD FOR DETERMINING DNA SEQUENCES

[75] Inventors: Rudy J. Dam, Lincoln University, Pa.; James E. Davis, Wilmington, Del.; Alan M. Hochberg, Hockessin, Del.; James M. Prober, Wilmington, Del.

[73] Assignee: E. I. Du Pont de Nemours and Company, Wilmington, Del.

[21] Appl. No.: 545,746

[22] Filed: Jun. 29, 1990

[51] Int. Cl.$^5$ .............................................. G01N 30/00
[52] U.S. Cl. .............................. 364/498; 364/571.02; 364/487
[58] Field of Search ............... 364/498, 484, 485, 486, 364/487, 555, 554, 551.01, 550, 571.01, 571.02, 571.05, 497, 496, 413.1, 413.07–413.09; 250/458.1; 324/77 R, 77 A, 77 B; 435/6; 935/77; 73/23.36, 61.1 C

[56] References Cited

U.S. PATENT DOCUMENTS

| | | | |
|---|---|---|---|
| 4,008,388 | 2/1977 | McLafferty et al. | 364/498 |
| 4,353,242 | 10/1982 | Harris et al. | 73/61.1 C |
| 4,833,332 | 5/1989 | Robertson et al. | 298/488.1 |
| 4,972,325 | 11/1990 | Hara | 364/497 |
| 5,014,217 | 5/1991 | Savage | 364/498 |

FOREIGN PATENT DOCUMENTS

| | | |
|---|---|---|
| 0157280 | 3/1985 | United Kingdom . |
| 0198403 | 10/1986 | United Kingdom . |
| 0294524 | 6/1987 | United Kingdom . |
| 0242629 | 10/1987 | United Kingdom . |
| 0294996 | 12/1988 | United Kingdom . |

OTHER PUBLICATIONS

Cedric I. Davern, The Genetic Code, published Oct. 1962, pp. 140–149.
S. Beck, Anal. Biochem., 164, pp. 514–520, Jan. (1987).
S. Beck, Nucleic Acids Res., 17, pp. 5115–5123 May (1989).
L. M. Smith, et al., Nucleic Acids Res., 13, pp. 2399–2412 Mar. (1985).
W. Ansorge, et al., J. Biochem. Biophys. Meth., 13, pp. 315–323 Sep. (1986).
H. Kambara, et al., Biotechnology, 6, pp. 816–821 Jul. (1988).
A. Savitsky, et al., Anal. Chem., 34, pp. 1627–1639 Jul. (1964).
L. C. Allen, et al., J. Chem. Phys., 40, pp. 3135–3141 Jun. (1964).
J. F. Muldoon, et al., "On-Line Computer Methods for Area Allocation of Unresolved Chromatograph Peaks" Mar. 1969.
IBM Contributed Program Library No. 1130-17.3002, IBM Corporation Mar. 1969.
P. Jansson, Deconvolution with Applications in Spectroscopy, Academic Press (1984).

Primary Examiner—Parshotam S. Lall
Assistant Examiner—M. J. Zanelli

[57] ABSTRACT

The method of this invention obtains the underlying peak shapes of two signal spectrums whose ratios are representative of different species. The underlying peak shapes are fitted to the signal spectrums in a way that yield accurate ratios. The ratios are accurate even when the location of the peaks are not precisely known.

8 Claims, 11 Drawing Sheets

METHOD FOR DETERMINING DNA SEQUENCES

CROSS REFERENCE TO RELATED APPLICATIONS

This application is related to inventions described in U.S. Pat. No. 4,833,332 entitled "Scanning Fluorescent Detection Systems", issued to Robertson et al. and to an application S.N. 07/057566, filed Jun. 12, 1987 by Prober et al. entitled "Method, System, and Reagents for DNA Sequencing".

FIELD OF THE INVENTION

This invention relates to a method for obtaining more accurate DNA sequence information.

BACKGROUND OF THE INVENTION

DNA sequencing is one of the cornerstone analytical techniques of modern molecular biology. The development of reliable methods for sequencing has lead to great advances in the understanding of the organization of genetic information and has made possible the manipulations of genetic material (i.e., genetic engineering).

There are currently two general methods for sequencing DNA: the Maxam-Gilbert chemical degradation method [A. M. Maxam et al., *Meth. in Enzvm.*, Vol. 65, 499-559 (1980)] and the Sanger dideoxy chain termination method [F. Sanger, et al., *Proc. Nat. Acad. Sci. USA*. Vol. 74, 5463-5467 (1977)]. A common feature of these two techniques is the generation of a set of DNA fragments which are analyzed by electrophoresis. The techniques differ in the methods used to prepare these fragments.

With Sanger's technique, DNA fragments are produced through partial enzymatic copying (i.e., synthesis) of the piece of DNA to be sequenced. In the most common version, the piece of DNA to be sequenced is inserted, using standard techniques, into a "sequencing vector", a large, circular, single-stranded piece of DNA such as the bacteriophage M13. This becomes the template for the copying process. A short piece of DNA with its sequence complementary to a region of the template just upstream from the insert is annealed to the template to serve as a primer for the synthesis. In the presence of the four natural deoxyribonucleoside triphosphates (dNTP's), a DNA polymerase will extend the primer from the 3'-end to produce a complementary copy of the template in the region of the insert. To produce a complete set of sequencing fragments, four reactions are run in parallel, each containing the four dNTP's along with a single dideoxyribonucleoside triphosphate (ddNTP) terminator, one for each base. ($^{32}$P-Labeled or fluorophore-labelled dNTP is added to afford labeled fragments.) If a dNTP is incorporated by the polymerase, chain extension can continue. If the corresponding ddNTP is selected, the chain is terminated. The ratio of ddNTP to dNTP's is adjusted to generate DNA fragments of appropriate lengths. Each of the four reaction mixtures will, thus, contain a distribution of fragments with the same dideoxynucleoside residue at the 3'-terminus and a primer-defined 5'-terminus.

In both the Sanger and Maxam-Gilbert methods, base sequence information which generally cannot be directly determined by physical methods has been converted into chain-length information which can be determined. This determination can be accomplished through electrophoretic separation. Under denaturing conditions (high temperature, urea present, etc.), short DNA fragments migrate as if they were stiff rods. If a gel matrix is employed for the electrophoresis, the DNA fragments will be sorted by size. The single-base resolution required for sequencing can usually be obtained for DNA fragments containing up to several hundred bases.

To determine a full sequence, the four sets of fragments produced by either Maxam-Gilbert or Sanger methodology are subjected to electrophoresis. This results in the fragments being spatially resolved along the length of the gel. One method of discriminating the dyes (which replace the $^{32}$p label) and using this information to determine DNA sequences is described in the Prober et al. application and it is available in a commercial instrument known as the Genesis#2000 available from E. I. du Pont de Nemours and Company, Wilmington, Delaware. The Genesis TM system for sequencing DNA, comprising a means for detecting the presence of radiant energy from closely-related yet distinguishable reporters or labels, which are covalently attached to compounds which function as chain terminating nucleotides in a modified Sanger DNA chain elongation method. Distinguishable fluorescent reporters are attached to each of the four dideoxynucleotide bases represented in Sanger DNA sequencing reactions, i.e., dideoxynucleotides of adenine, guanine, cytosine, and thymine. These reporter-labeled chain terminating reagents are substituted for unlabeled chain terminators in the traditional Sanger method and are combined in reactions with the corresponding deoxynucleotides, an appropriate primer, template, and polymerase. The resulting mixture contains DNA fragments of varying length that differ from each other by one base which terminate on the 3' end with uniquely labeled chain terminators corresponding to one of the four DNA bases. This new labeling method allows elimination of the customary radioactive label contained in one of the deoxynucleotides of the traditional Sanger method.

Detection of these reporter labels can be accomplished with two stationary photomultiplier tubes (PMT's) which receive differing wavelength bands of fluorescent emissions from laser-stimulated reporters attached to chain terminators on DNA fragments. These fragments can be electrophoretically separated in space and/or time to move along an axis perpendicular to the sensing area of the PMT's. The fluorescent emissions first pass through a dichroic filter having both a transmission and reflection characteristic, placed so as to direct one characteristic (transmission) to one PMT, and the other characteristic (reflection) to the other PMT. In this manner, different digital signals are created in each PMT that can be ratioed to produce a third signal that is unique to a given fluorescent reporter, even if a series of fluorescent reporters have closely spaced emission wavelengths. This system is capable of detecting reporters which are all efficiently excited by a single laser line, such as 488 nm, and which have closely spaced emissions whose maxima usually are different from each other by only 5 to 7 nm. Therefore, the sequential base assignments in a DNA strand of interest can be made on the basis of the unique ratio derived for each of the four reporter-labeled chain terminators which correspond to each of the four bases in DNA.

While the base information is contained in fluorescent labels in the Genesis TM 2000 unit, it is noted that the information could also be contained in a colorimetric label (S. Beck, *Anal. Biochem.* 164 (2) 514-520 (1987)), chemiluminescent (S. Beck, *Nucleic Acids* 17 5115-5123 (1989)) or other signal.

Figure 1:
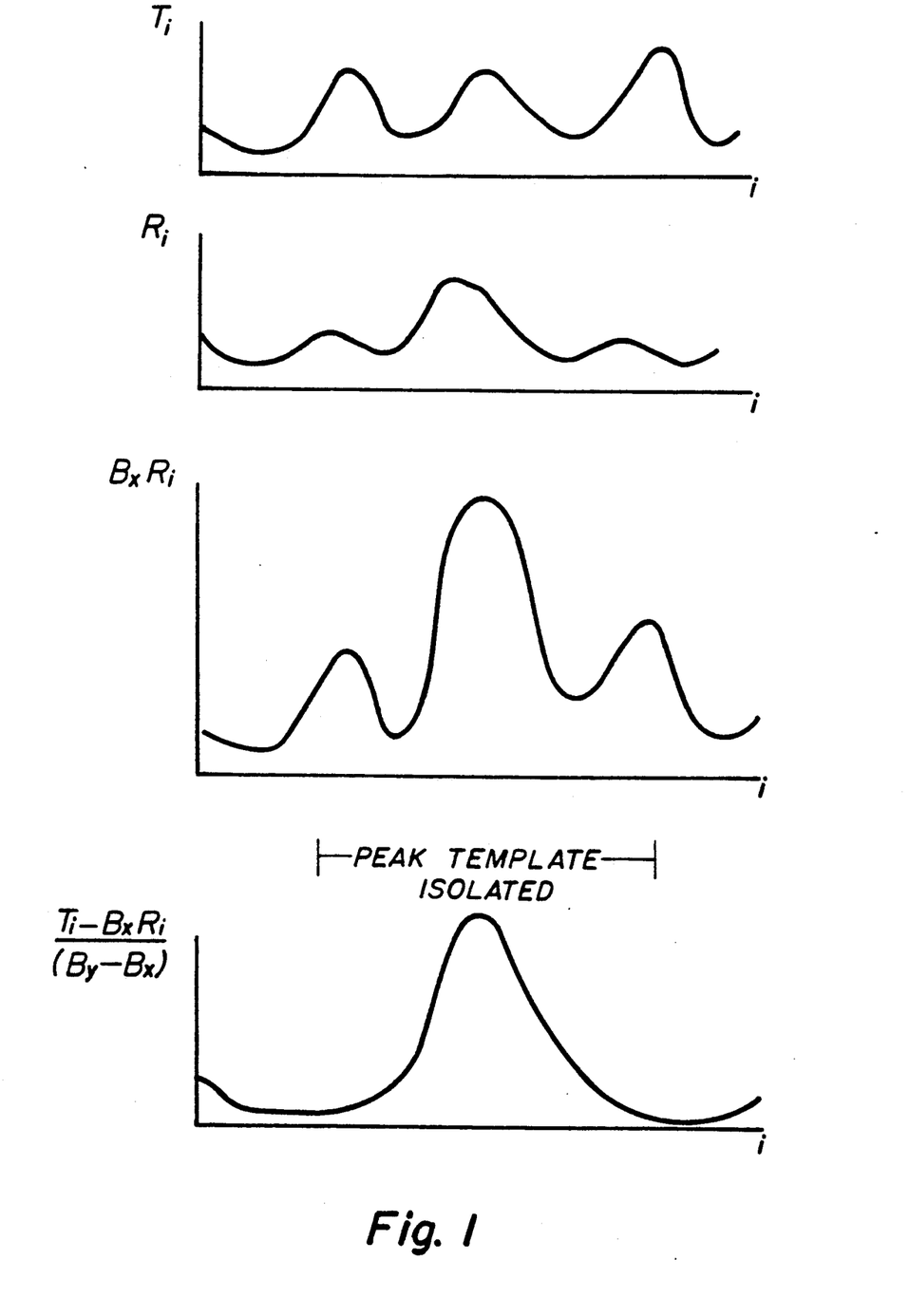
FIG. 1 shows a representation of the two signals plotted against time illustrating the technique by which the peak template is obtained.

The Genesis TM DNA sequencer is designed to take advantage of the dideoxy chain termination chemistry. In order to employ this chemistry, it was necessary to use four chemically-similar dyes to distinguish the four bases A, C, G, and T. This selection of dyes led to a two-channel detection scheme, in which the ratio of two signals is used to determine which base has passed the detector. When peaks are well-resolved and noise-free, the ratiometric signals are easy to interpret (FIG. 1). However, to maximize the amount of sequence information that can be obtained from each run, it is necessary to accurately interpret the two-channel signal under conditions of poor peak resolution and significant noise.

The methods for analysis of two-channel data under these conditions differ from those used to process conventional electrophoretograms and chromatograms. The output of the analysis described here is a sequence of base identifications, A, C, G, or T, while in chromatography, the desired output is typically a list of peak positions and areas. Chromatographic processes generally do not involve two detector signals coupled by one of four ratios. This relationship between the two signals is a special property of the sequencer described in the Prober et al. patent application. Computational efficiency is a more important consideration for sequencing than for chromatography. In chromatography, useful results can be obtained by performing extensive computations on two or three peaks; in sequencing, it may be necessary to analyze 300 to 600 peaks.

The ratiometric scheme of Prober et al also presents a signal interpretation problem different from that of other DNA sequencers. Sequencers employing primer chemistry are described in [L. M. Smith et al. *Nucleic Acids Res.* 2399-2412 (1985) and W. Ansorge et al. *J. Biochem. Biophys. Meth.* 13 315-323 (1986)]. These sequencers employ four signal channels, one for each base. Other sequencers, such as that described by Kambara et al. [H. Kambara et al., *Biotechnology* 6 816-821 (1988)], employ one signal in each of four electrophoresis lanes These systems employ yet another class of data analysis methods, since the results from four separate lanes must be registered, or aligned, in the proper time sequence.

Although modifications to standard methods are necessary, analysis methods that are applicable to the processing of two-channel DNA sequencing data make use of results in the chromatography literature. These are reviewed below.

Digital smoothing [A. Savitsky et al., *Anal. Chem.* 34 1627-1639 (1964)]can be applied to remove noise from fluorescent signals. Digital differentiation, also described by Savitsky and Golay, can be used to aid in peak finding, but does not provide a means for interpreting ratiometric data under conditions of poor resolution.

Digital filtering [L. C. Allen et al., *J. Chem Phys.* 40 3135-3141 (1964)]can be used to improve peak-finding accuracy where there is a priori information regarding the peak shape.

Standard chromatographic baseline removal techniques [J. F. Muldoon et al., "On-Line Computer Methods for Area Allocation of Unresolved Chromatograph Peaks", Pittsburgh Conference on Analytical Chemistry and Applied Spectroscopy", March 7, 1969, Cleveland, OH; K. J. Burkhardt, "General Purpose Chromatograph Peak Integration Program", IBM Contributed Program Library No. 1130-17.3.002, IBM Corporation (1968)]can give fair performance under some conditions. However, sequencing signals of interest have a larger dynamic range and poorer resolution than is generally accepted for chromatograms. When a small peak occurs next to a large one, baseline removal methods can introduce substantial error in ratio calculation, and thereby result in sequencing errors.

Digital filtering and deconvolution [P. Jansson, *Deconvolution with Applications in Spectroscopy*, Academic Press (1984)]are methods used to enhance the resolution of chromatograms. Both were unsuccessful in enhancing sequencing performance of the ratiometric scheme of Prober et al. Both methods tend to amplify noise in proportion to their ability to enhance resolution; significant resolution enhancement came along with an unacceptable signal-to-noise ratio. Both methods gave oscillating signals which produced peaks in the waveform where none were supposed to exist. These additional peaks can be erroneously interpreted as extra bases inserted into a sequence. Such frequent insertion errors are unacceptable, since they alter the entire biological meaning of a sequence that encodes a protein [C. I. Davern, *Genetics: Readinos from Scientific America*, W. H. Freeman & Co., Inc. 142-149 (1986)]. Deconvolution introduced further error into the ratio-determining process, since the signal peak shape varies during the run, causing the deconvolving "kernel function" to become inaccurate.

The sequencer described in Prober et al utilizes a combination of the methods above for signal interpretation. Signal processing began with a 9-point Savitsky-Golay smoothing of both detector channels, to reduce noise. The sum of the two channels were then passed through a digital filter, which approximated a smoothing, second-derivative operator. A positive-going peak in the resultant data was interpreted as a peak in the original signals, corresponding to a DNA base. The zero-crossings of the resultant peak were interpreted as the inflection points of the corresponding peak in the original signals. A straight line between the inflection points was taken as the peak baseline, and the ratio of areas above the baseline in the two channels of resultant data was interpreted to determine the base sequence.

This method suffered from a number of disadvantages. The determination of baseline and peak area was subject to interference from adjacent peaks, which would be 10-100-fold greater in size than the peak of interest. Additionally, the method gave no reliable indication of such interference, so that there was no way to "flag" potentially erroneous base calls. These phenomena combined to limit the useful run length of the sequencer to approximately 300 bases, after which point limited resolution and signal-to-noise ratio led to an unacceptable sequence error rate. Furthermore, within the first 300 bases, there is a persistent phenomenon of anomalously high mobility of DNA fragments ending in a GC sequence. This causes C peaks to move closer to preceding G peaks, resulting in poor resolution of the pair and additional base calling errors.

SUMMARY OF THE INVENTION

Many of the disadvantages of these prior techniques for selecting the proper bases in order to accurately obtain the ratios and hence "call" the various bases in sequence are overcome by the method of this invention.

In short, the sequence of bases may be determined, i.e., "called", if the underlying peak shape is known throughout the run. According to this invention, the underlying peak shape is periodically redetermined and fitted to the data in a way that yields accurate ratios. The method insures that more accurate ratios are obtained even when the precise location of the peak is not known. Also the method contains self-consistency checks so that potentially erroneous ratios and hence base determinations may be recognized.

The invention finds use in a method for obtaining signals characteristic of different species following the species separation in time and/or space and determining the identity of such species, the method including generating a first signal that varies in amplitude in a first sense to form peaks as a function of the nature of the species, generating a second signal that varies in amplitude in a second sense different than the first sense to form peaks as a function of the nature of the species, any peak of the first and second signals being representable by the sum of three peak templates, and obtaining a third signal corresponding to the ratio of a function of the peaks in the first and second signals, the amplitude of the third signals being indicative of the identity of each of the species, the improvement wherein the third signals are obtained by the steps of: first using a provisional template as describe later as a "bootstrap", finding a sequence of peaks XYX in corresponding regions of the first and second signals where X represents one species and Y represents another species, subtracting a multiple of the first signal from the second signal over time from approximately the peak center of the first X to approximately the peak center of the second X such that the X peaks in the difference signal are substantially zero, thereby obtaining a prototypical template (the residual peak) for each signal, and subsequently fitting the template by least squares to the respective first and second signals to obtain the amplitude of the peak of the first and second signals for obtaining the third signal.

Further in accordance with this method, the template for each signal may be shifted forward and backward with respect to time and fitted by least squares to each signal. In accordance with another aspect of the invention, derivative template peaks are obtained and the combination of peaks and derivative peaks that least squares fit each signal is obtained, thereby to determine the signal peaks of each signal by more accurately accounting for time jitter.

BRIEF DESCRIPTION OF THE DRAWINGS

The invention may be easily understood by considering the following drawings in connection with the written description in which.

DETAILED DESCRIPTION OF THE PREFERRED EMBODIMENT

The method of this invention will be described in conjunction with the Genesis TM 2000 Sequencer which has two detectors which provide the two output signals R and T as described above. Note the first and perhaps the most necessary step in the method of this invention is to attain the underlying peak shape so that a representative peak shape may be fitted to the data derived from the detector signal to yield more accurate ratios. The problem arises in that the shape of the peaks change as the electrophoresis process continues. When a measured peak say Y, which could be any of the four peaks corresponding to a base (A, C, T or G), is preceded and followed by peaks representing some other base, say X, then a multiple of the R channel is subtracted from the T channel so that the size of the X peaks and the difference spectrum are minimized. This leaves the Y peak in a difference signal which is an ideal peak shape to use for the template because it looks almost exactly like the measured peaks.

This may be perhaps more easily understood with reference to FIG. 1 in which the two channels from the respective detectors labeled $T_i$ and $R_i$ plotted versus the time index i, as the abscissa.

The following notations will be used in this description: the two detector signals will be designated R and T, where $R_i$ and $T_i$ represent the $i^{th}$ data point of the digitized signal. Let $c_j = i$ represent the center of the $j^{th}$ base peak at index value i. The prime (') will designate a derivative with respect to the index variable which can be calculated as needed by the method of Savitsky above. Pk will represent the $k^{th}$ data point of the peak template, i.e., the idealized peak shape function. This function will be centered at k=0, and will cover $-N_p < = k < = N_p$.

The ratio of detector signals for the four bases T, C, A, and G will be denoted as $\beta_T$, $\beta_A$, and $\beta_G$, respectively. Thus for an isolated, noiseless C peak, for example, the R and T waveforms would have the relationship $T_i = \beta_C \cdot R_i$, for $i$ covering the range of the peak.

Peak shape is not constant, but varies gradually throughout the run. Therefore, a peak template must be undated periodically. The two-channel data provides a unique opportunity to extract such a peak template, even when resolution is extremely poor. This ability to extract a template is based on the mathematical manipulation of two-channel date, and cannot be generally applied to other chromatographic or electrophorectic processes.

Under most conditions, DNA sequences can be assumed to be a random series of A's, C's, T's and G's. Under this assumption, approximately once every sixteen based the sequence will take the form "XXX", when "X" represents one base (A, C, T, or G), and "Y" represents a different base. When this occurs, the signals have the form:

$$T_i = a_{j-1} \cdot \beta_x \cdot P_{i-c(j-1)} + a_j \beta_y P_{i-c(j)} \cdot \beta_x \cdot P_{i-c(j+1)}$$

$$R_i = a_{j-1} \cdot P_{i-c(j-1)} + a_j \cdot P_{i-c(j)} + a_{j+1} \cdot P_{i-c(j+1)}$$

where the "Y" peak is peak j, and the a's represent peak amplitudes. The range of i covers peaks $j-1$, j and $j+1$. The influence of the $j-2^{th}$ and $j+2^{th}$ peaks and all others are assumed negligible. Under these assumptions:

$$\frac{T_i - \beta_x R_i}{(\beta_Y - \beta_X)} = a_j P_{i-c(j)}$$

gives an isolated peak template centered at c(j), having amplitude $a_j$ (FIG. 1).

In practice, a "bootstrap", or self-starting procedure is used. The procedure starts with an initial (Gaussian) approximation to the shape function P. Several bases are called until an "XYXZ" sequence occurs, and then use the formula above to update P. This works well because the signals at the start of a run are generally well-resolved. Accurate base calling at that stage of the run is not dependent on an extremely accurate approximation for P.

Further in accordance with this invention a curve fitting procedure is used instead of the prior art processes of deconvolution or derivative peak height. In this new incremental curve fitting process, the detector signals which represent the sequence of peaks constituting each detector output is matched as closely as possible by a synthetic spectrum starting with the peak template obtained as described above. Copies of the peak template are then combined in varying sizes or amount and position (the peak template is shifted forward and backward and varied in amplitude). The best combination of size and position is found from a statistical procedure known as least squares. When this is done the size of the peaks in the synthetic signals of the two channels represent the amount of light in the measured signal without the interference from neighboring peaks. The ratio of these sizes indicates which base constituted that peak.

The least squares procedure subtracts the synthetic signal, derived from the peak template, from the signal derived from the detectors. The resulting difference is a flat line if the signals are perfectly matched. Usually the difference is not zero, but has some positive going peaks and some negative going peaks. To alleviate the effect of the negative peaks, the values in the difference signal are squared so that the difference peaks are always positive and cannot cancel. The area of the squared difference signal is called sum-of-the-squares. By adjusting the amount (amplitude) of each copy of the template, the sum-of-the-squares will be varied. The "best" amounts of each copy of the template are those for which the least sum-of-the-squares is achieved. When this is done, the ratio of the peak sizes of the peaks from the two channels is indicative of the base.

Figure 2:
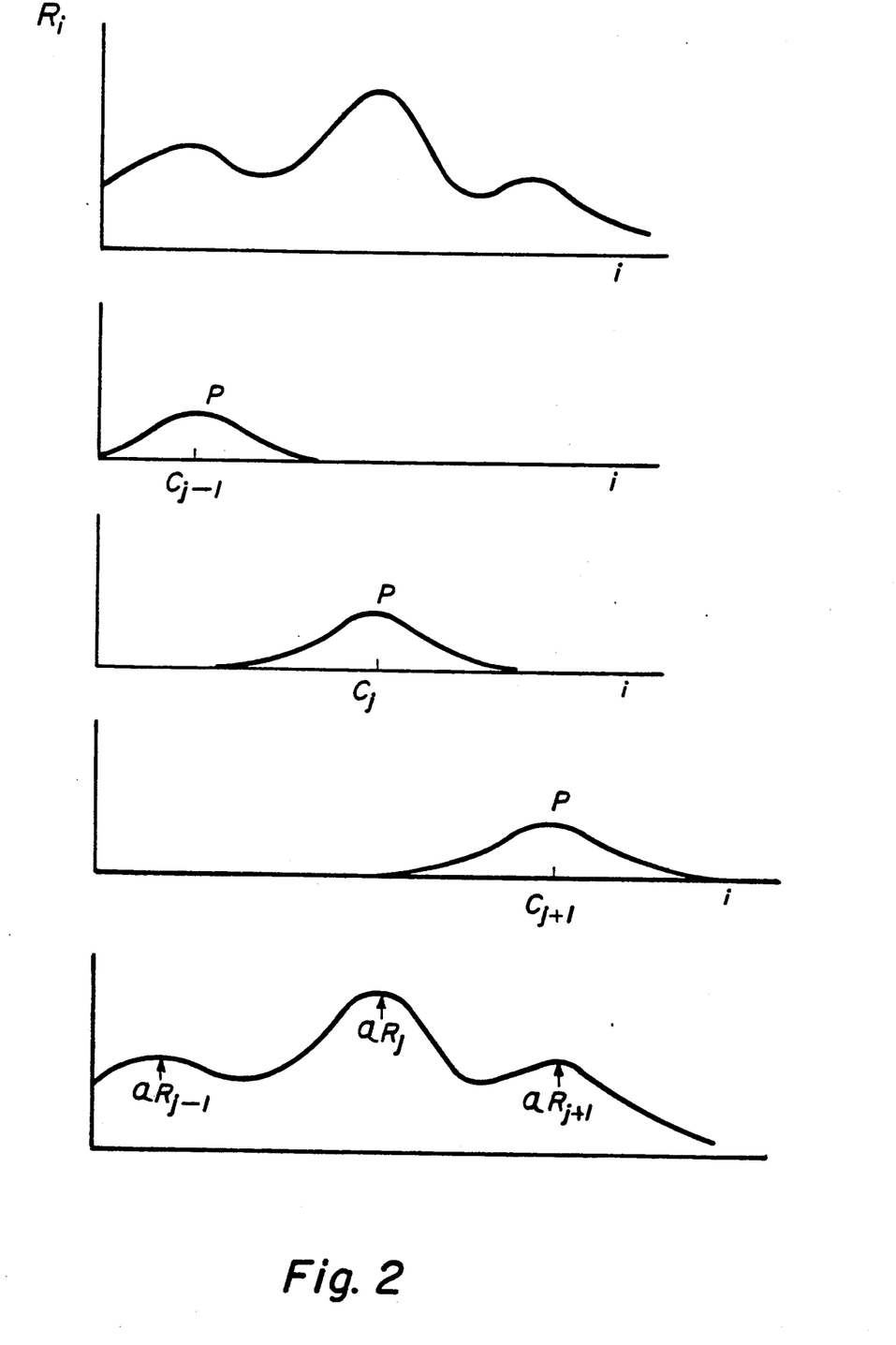
FIG. 2 depicts a technique by which copies of the peak template are shifted forward and backwards along the time scale to form a composite peak template.
Figure 3:
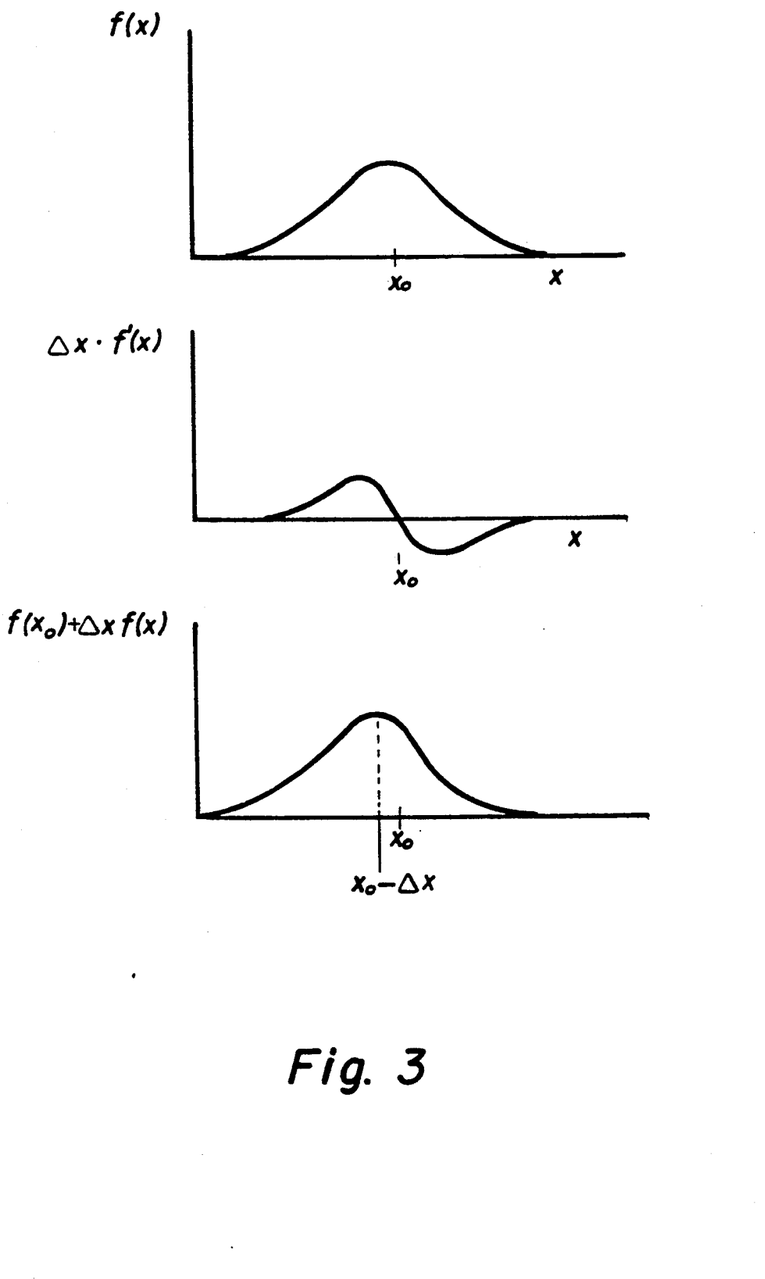
FIG. 3 shows several curves depicting the derivative of the peak template and summation of the peak template and its derivative plotted as a function of time illustrating the manner in which the peak template is time shifted.

An understanding of these procedures is perhaps better understood with reference to FIGS. 2 and 3. In FIG. 2, the amplitude of a detector signal, say R is plotted against time designated i. The size and position of the peaks in a synthetic signal is shifted along a time scale. The peak template is shifted both one unit in time backward and another unit in time forward as depicted in FIG. 2 wherein the designation $c_{j-1}$ designates the peak backward shifted in time and $c_{j+1}$ signifies the forward shift in time. The summation of these peaks is shown in the bottom drawing of FIG. 2 in which the several waveforms are designated and depicted to provide a composite peak template.

Assuming peak center positions are known, and a locally-accurate composite peak template P exists, the R and T channel amplitudes of an uncalled peak can be determined by a linear least-squares fit [G. E. P. Box, et al., *Statistics for Experimenters*, John Wiley & Sons, Inc., 501–502 (1978)] of a sum of appropriately shifted templates to the data:

Find $aR_{j-1}$, $aR_j$, $aR_{j+1}$, $aT_{j-1}$, $aT_j$, $aT_{j+1}$
To minimize the sum for $i = c_{j-1}$ to $c_{j-1}$ of:
$(R_i - r_i)^2$ and $(T_i - t_i)^2$
where:
$r_i = aR_{j-1} P_{i-c(j-1)} + aR_j P_{i-c(j)} + aR_{j+1} P_{i-c(j+1)}$
$t_i = aT_{j-1} P_{i-c(j-1)} + aT_j P_{i-c(j)} + aT_{j+1} P_{i-c(j+1)}$.

Then the ratio $\beta_j = aTj/aRj$ can be used to determine the base for peak j (FIG. 2). When this method is used, the adjacent poorly-resolved peaks, peaks $j-1$ and $j+1$, cause lease interference with the ration determination and gives more accurate base calling of peak j. The method can be extended to fit more than 3 peaks, but this has not been found to enhance accuracy enough to justify the increased computational load.

The least square fit linear regression equations can be expressed in matrix form as:

$$\Theta = (X^T X)^{-1} X^T Y$$

$$\text{Where } \Theta = \begin{bmatrix} aR_{j-1} \\ aR_j \\ aR_{j+1} \end{bmatrix} \text{ or } \begin{bmatrix} aT_{j-1} \\ aT_j \\ aT_{j+1} \end{bmatrix}$$

$Y = R_{i-c(j-1)}$ or $T_{i-c(j-1)}$ for $i = C_{j-1} \ldots C_{j+1}$
$X = [X_{ik}] = [P_{i-c(j+k-2)}]$ for $k = 1 \ldots 3$.

The method specified up to this point is susceptible to errors resulting from the determination of the peak center positions $c_j$. Peak finding by digital filtering is subject to interference from adjacent, poorly-resolved peaks, is noise-sensitive, and subject to index quantification errors. One potential remedy for this problem is to search for values of $c_{j-1}$, $c_j$, and $c_{j+1}$ to give the best least-squares fit as above. This, however, would be too computation-intensive to handle several hundred peaks on a desk top computer in a reasonable time.

In accordance with another aspect of this invention, the process of adjusting the position of peaks in the synthetic spectrum may be simplified by combining copies of the derivative of the template into the synthetic spectrum. The derivative template is formed from the peak template and used to fine tune the synthetic spectrum. By adding the derivative of the peak template to each peak forming the composite template, the peak positions can be shifted a small amount to achieve a better least squares fit as illustrated in FIG. 3.

In short, the peak position problem can be solved effectively by using the derivative of the peak template function P to "fine-tune" the peak location to an optimum. The first term of a Taylor-series expansion [G. B. Thomas, *Calculus and Analytic Geometry*, Addison-Wesley, 632–635 (1969)] of P is:

$$P(X_0 + \beta x) = P(X_0) + \beta x \cdot P'(X_0)$$

which can be interpreted as follows: adding a small amount, $\Delta x$, of a derivative to the peak shape function has the effect of shifting it along the x axis by an amount $\Delta x$. This shifting can be used as long as the first-term approximation holds, that is, as long as $\Delta x^2 \cdot P''(X_0)$ is small.

In FIG. 3, the peak template is depicted in the top curve and is plotted against x as the abscissa having a peak center at $x_0$. The first derivative of f(x) is depicted in the second curve. The summation of the two curves is depicted in the bottom drawing of FIG. 3 in which it will be noted that the center of the peak formerly at xo has been shifted xo−Δx.

An extremely efficient implementation of this solution to the peak position problem, then, is to fit the R and T channels to the sum of three shifted peak templates and their three derivatives. This can be done with the same simple matrix calculation:

$$\Theta = (X^T X)^{-1} X^T Y$$

Where $\Theta = \begin{bmatrix} aR_{j-1} \\ \Delta R_{j-1} \\ aR_j \\ \Delta R_j \\ aR_{j+1} \\ \Delta R_{j+1} \end{bmatrix}$ or $\begin{bmatrix} aT_{j-1} \\ \Delta T_{j-1} \\ aT_j \\ \Delta T_j \\ aT_{j+1} \\ \Delta T_{j+1} \end{bmatrix}$ $Y = R_{i-c(j-1)}$ or $T_{i-c(j-1)}$ for $i = c_{j-1} \ldots c_{j+1}$ as before, and now
$X = [X_{ik}] = [P_{i-c(j+(k-3)/2)}]$ $k$ odd] for $k = 1,3,5$
$[P_{i-c(j+(k-4)/2)}]$ for $k = 2,4,6$ The base for peak j is again determined from the ratio $aT_j/aR_j$.

Two additional benefits of the peak-template method are noteworth. First, the linear regression provides a variance-covariance matrix $V=(X^T X)^{-1}$. The appropriate element of V gives the variances of $aR_j$ and $aT_j$, from which the variance of the ratio $\Delta j$ can be calculated:

$$V(\Delta_j) = [aT_j V(aR_h) + aR_j V(aT_j)]/aR_j^2$$

This gives a meaningful confidence measure for the base call; potentially erroneous calls can be flagged, based on their large variance of $\beta_h$.

Second, the template can itself be used to more accurately estimate the location of subsequent peaks prior to least squares refinement. This is done by searching the two signals for occurrences of a pattern matching the peak template. This matched-filter method of pattern recognition is described in [A. Rosenfeld, *Digital Picture Processing*, Academic Press, 296-306 (1976)].

Flowchart

The operation of the method of this invention will be more easily understood when considered in conjunction with the flowchart which may be used to derive a computer program. The flowchart appears in FIGS. 4A through 4H.

Figure 4A:
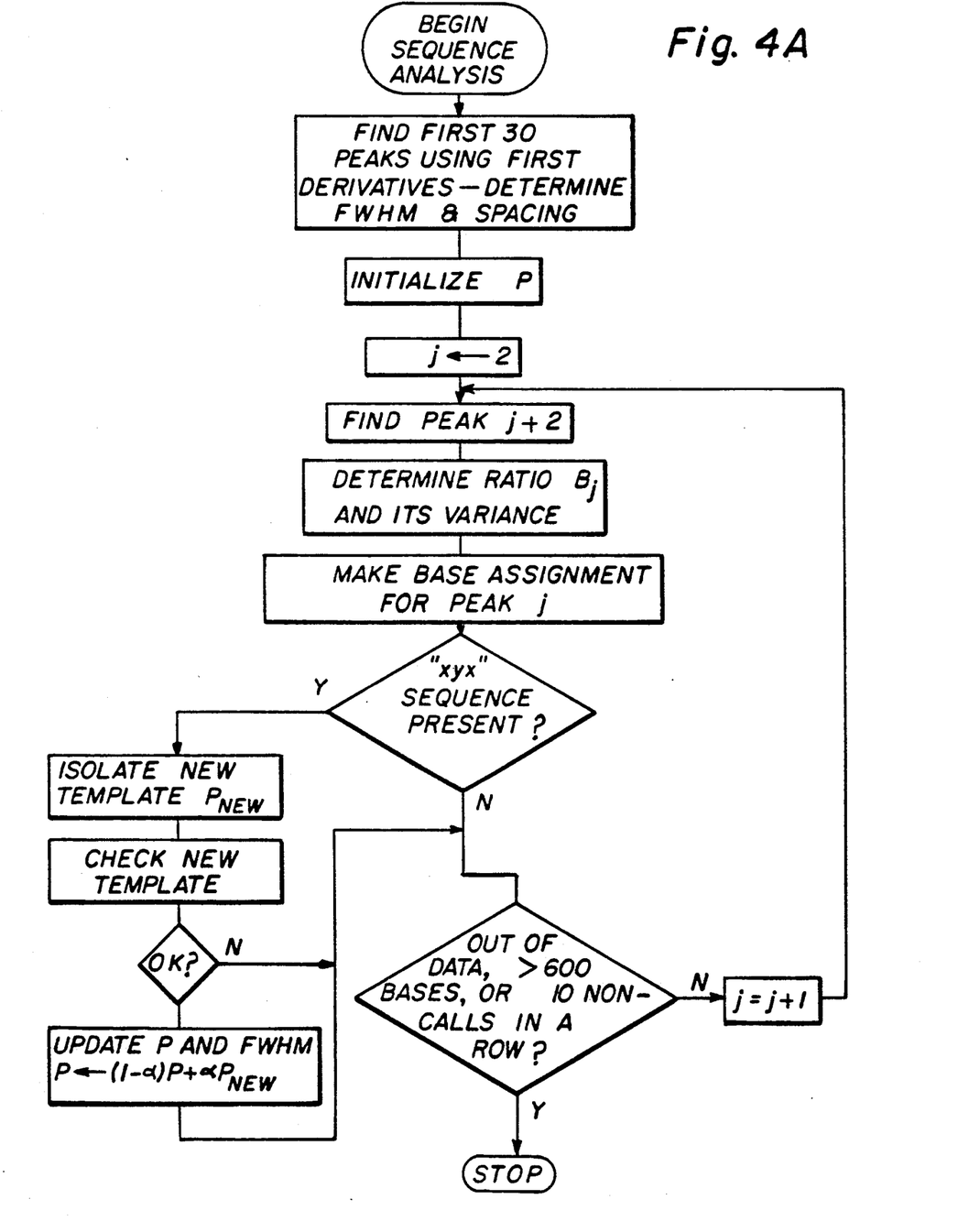
FIGS. 4A through H constitute a flow chart describing the method used in accordance with this invention.

FIG. 4A shows an overview of the template-based sequence analysis procedure. The $R_i$ and $T_i$ arrays are input to the process; their derivatives $R_i$ and $T_i$ are calculated using the method of Savitsky and Golay cited. An initial template width and average peak spacing is first determined by sampling the first thirty peaks present in the data, as described further in FIG. 4B. Then the main loop is entered. On each pass through the loop, one (central) peak is analyzed. The channel ratio for the peak is determined, and a base assignment is made. Following the base assignment, the growing sequence string is checked to see if a sequence of the form "XYX" has been detected. If so, a new peak template is formed. Otherwise, base calling proceeds until the data runs out or becomes unintelligible.

Figure 4B:
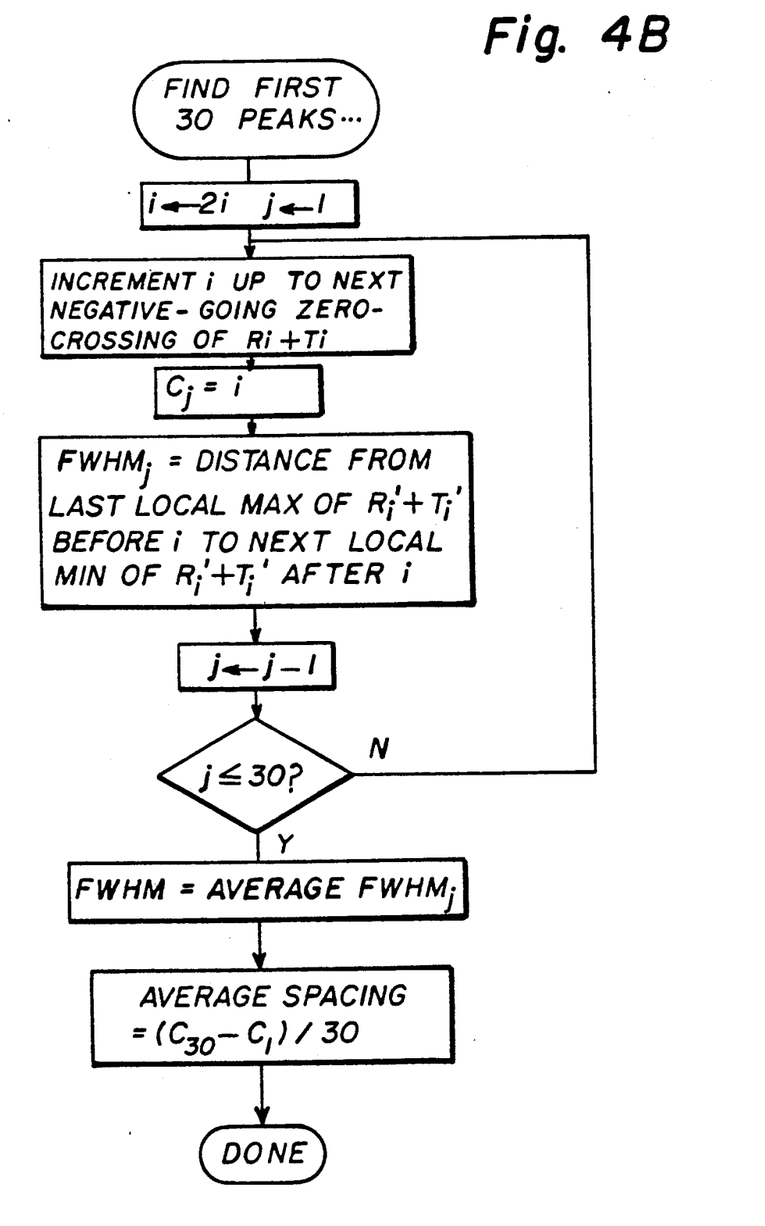
Figure 4C:
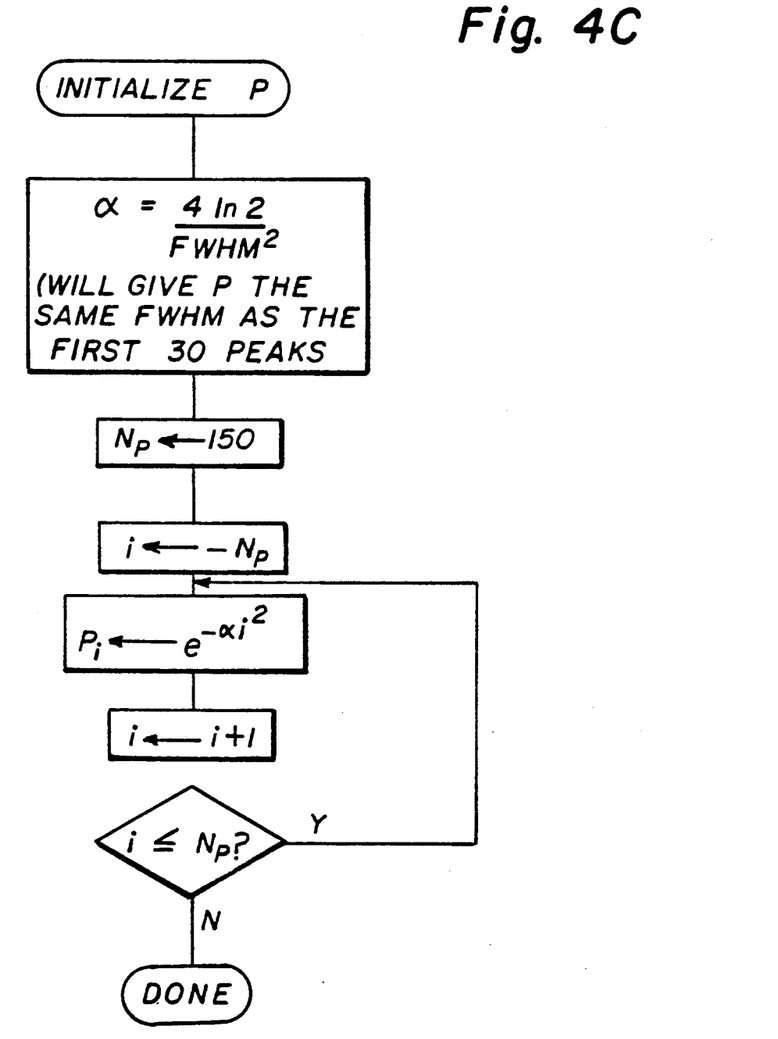

FIG. 4B shows the initialization process. A loop is used to locate negative-going zero-crossings of the summed channels. This indicates the location of a peak. This simple peak finding method can be used on the first thirty peaks because it is effective early in the run, when the data is well resolved and the signals are strong. The full-width at half-maximum (FWHM) for the peak is approximated by measuring the distance from the positive-going peak preceding the detected zero-crossing to the negative-going peak following the zero-crossing. The peak spacing from zero-crossing to zero-crossing is also calculated. FWHM and spacing are averaged for the first thirty peaks, and these parameters are used to generate an initial template P, as described in 4C.

FIG. 4C shows the generation of an initial template P. P is given a Gaussian form with unit amplitude and a mean of zero. The width parameter alpha of the Gaussian is given by the formula shown in Figure 4C. This formula gives P the same FWHM as that determined above for the first thirty peaks.

Figure 4D:
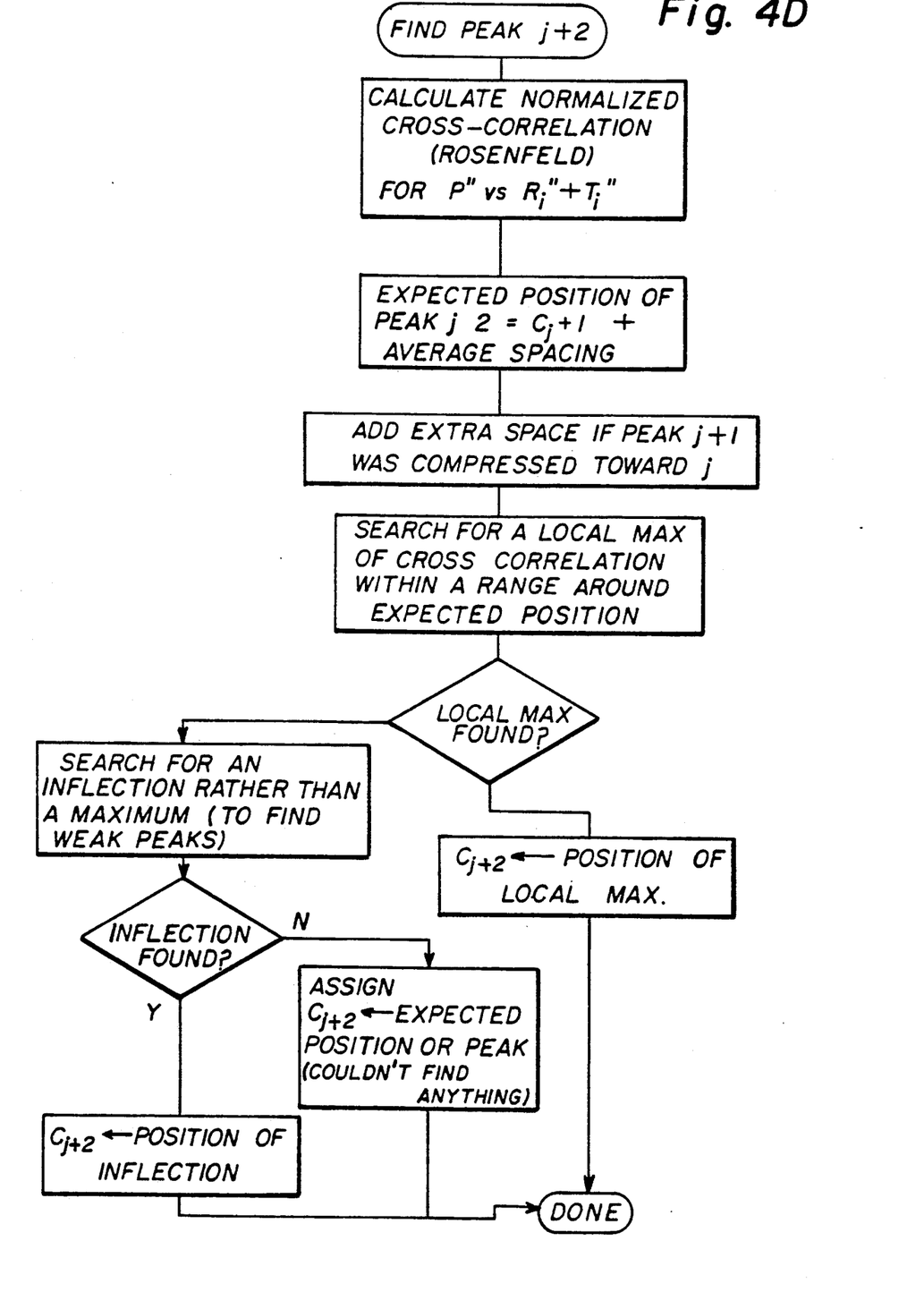

FIG. 4D shows the peak-finding process. The cross-correlation function is calculated between the peak template second derivative P" and the second derivative of the summed data channels. Then a search for a maximum of this function is started at the expected position of the next peak. This expected position is derived from the peak spacing and the position of the previous peak. If a local maximum of the cross-correlation function can be found within a reasonable range, say $\leq$FWHM, the position of the local maximum is taken to be the peak position. If no local maximum is found, the peak is very weak or badly compressed. A second search is carried out, this time for an inflection point in the cross correlation function. If an inflection point is found, it is taken to be the peak position. If neither a local maximum nor an inflection point is found, it is assumed that the peak is so weak as to be undetectable in which case a peak is assumed to exist at the expected peak position, and processing proceeds. If this were not done, the presence of a single missing peak would disrupt subsequent spacing and ratio calculations.

Figure 4E:
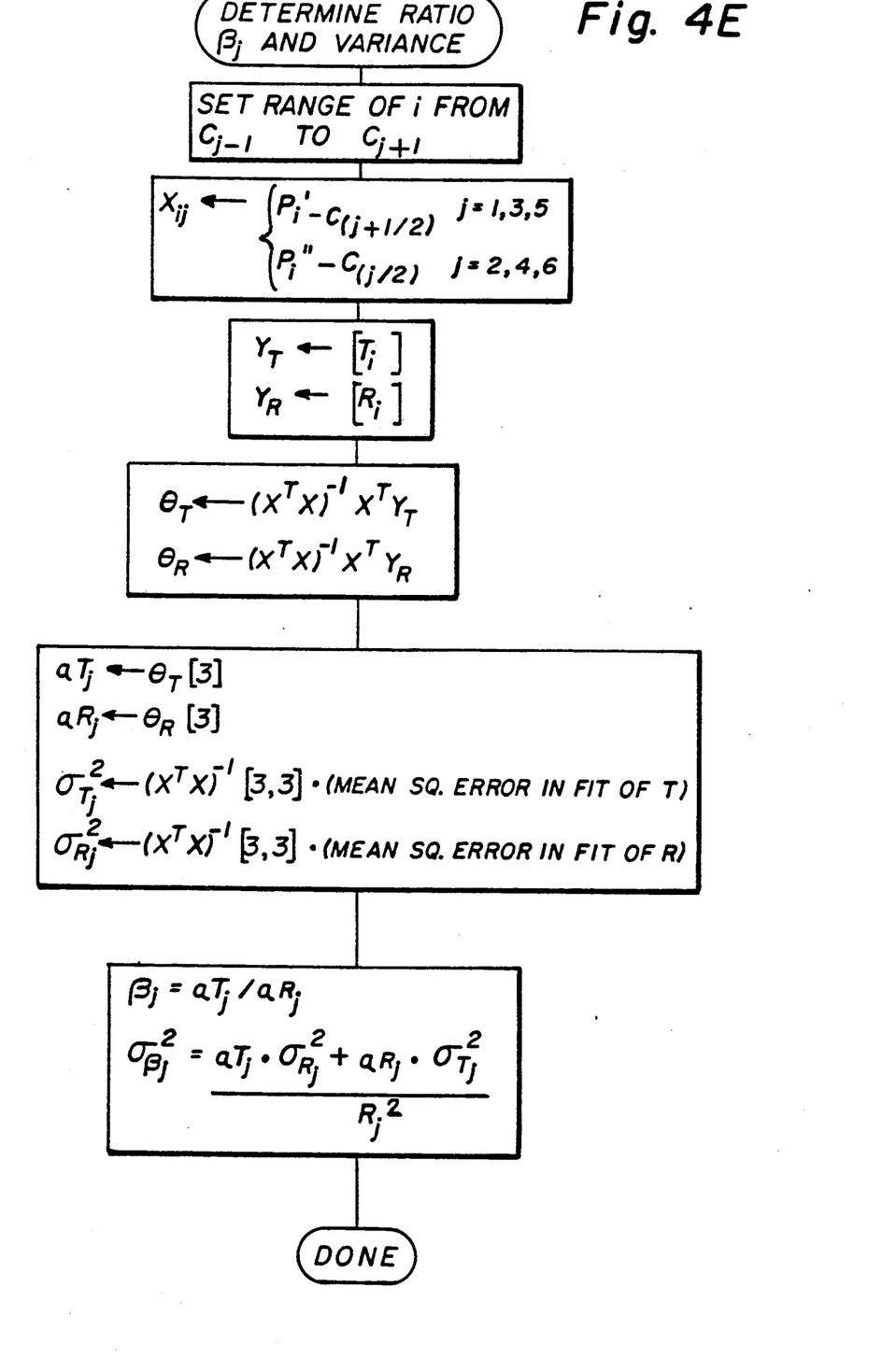

FIG. 4E shows the amplitude estimation and ratio calculation for a peak. The range of data used in this calculation goes from the previous peak center to the next peak center. The X matrix is formed from the peak templates and their smoothed derivatives. The odd rows of the X matrix contain the peak template for the previous, current, and next peak positions. The even rows contain the derivatives of the template for the previous, current, and next peak positions. The data is fit as the sum of the rows of X using the standard linear regression formulas shown. The mean squared error of the resulting fit is calculated, and used to determine the variance of the coefficients corresponding to the current peak in both channels. The ratio is calculated from these coefficients, and the variance of the ratio is calculated from the variance of these coefficients.

Figure 4F:
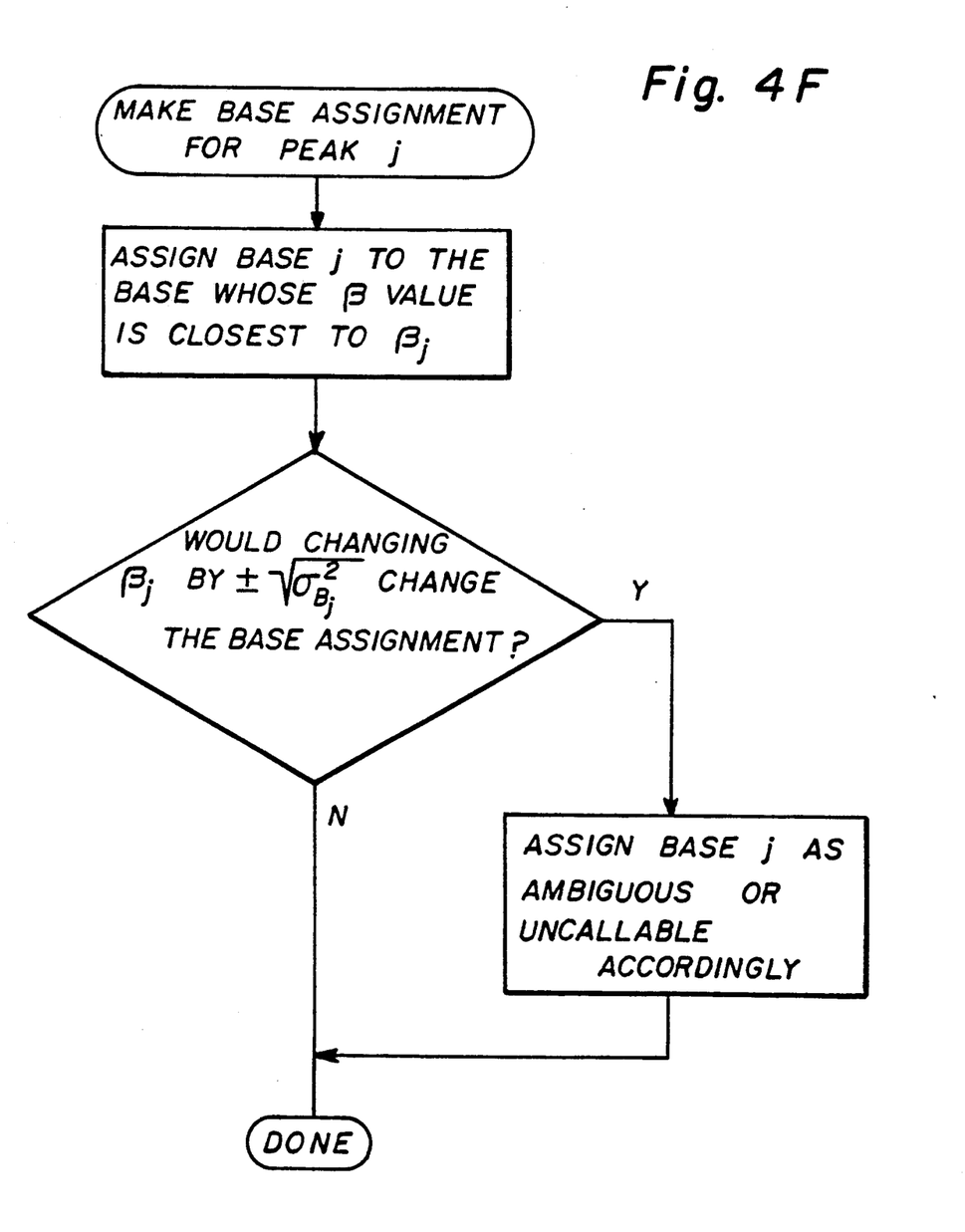

FIG. 4F describes how base assignments are determined from a ratio and its variance. The peak is assigned to a base whose ideal ratio most closely corresponds to the measured ratio. However, if changing the ratio by one standard deviation in either direction would change the base assignment, an ambiguous flag is attached to the assignment.

Figure 4G:
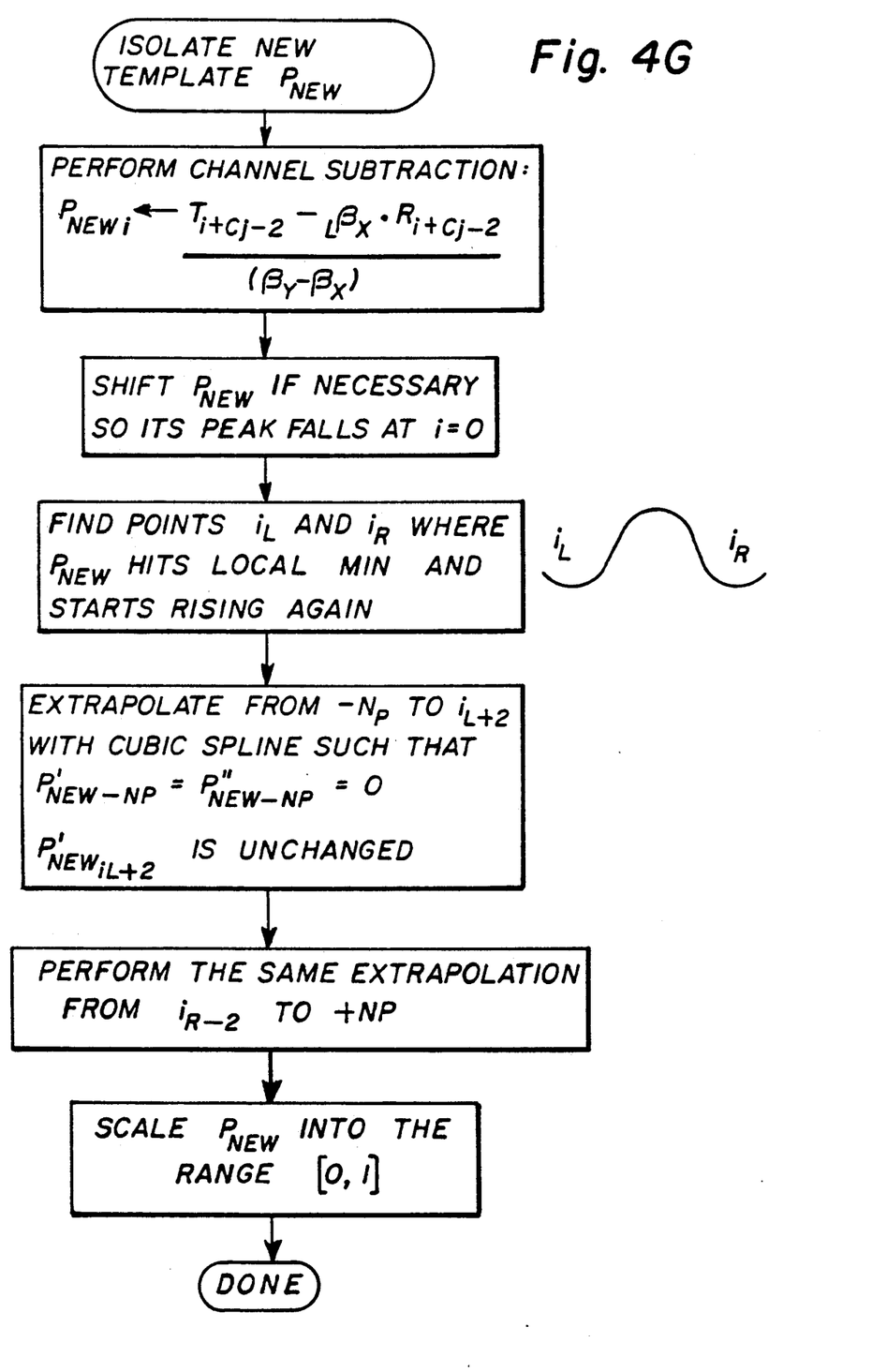

FIG. 4G shows the procedure for creating a new template. First the channels are subtracted in the proper ratio to eliminate the "X"peaks of the "XYX" sequence. This gives an isolated peak, with interference only from neighbors two peaks away. That peak is then shifted if necessary so that its local maximum falls in the center of the peak template array. Local minima to the left and right of the peak are located. From two data points inward from each local minimum, the peak is extrapolated by a cubic spline outward to the end of the peak template array. This process eliminates interference from the n−2 and n+2 neighbors. The cubic spline is chosen to match the derivative of the peak at the starting points of the spline, and to set the first and second derivatives of the template to zero at the ends of the peak template array. Following the extrapolation, the peak template array is scaled to cover the range [0,1], to create a provisional template ready for checking.

Figure 4H:
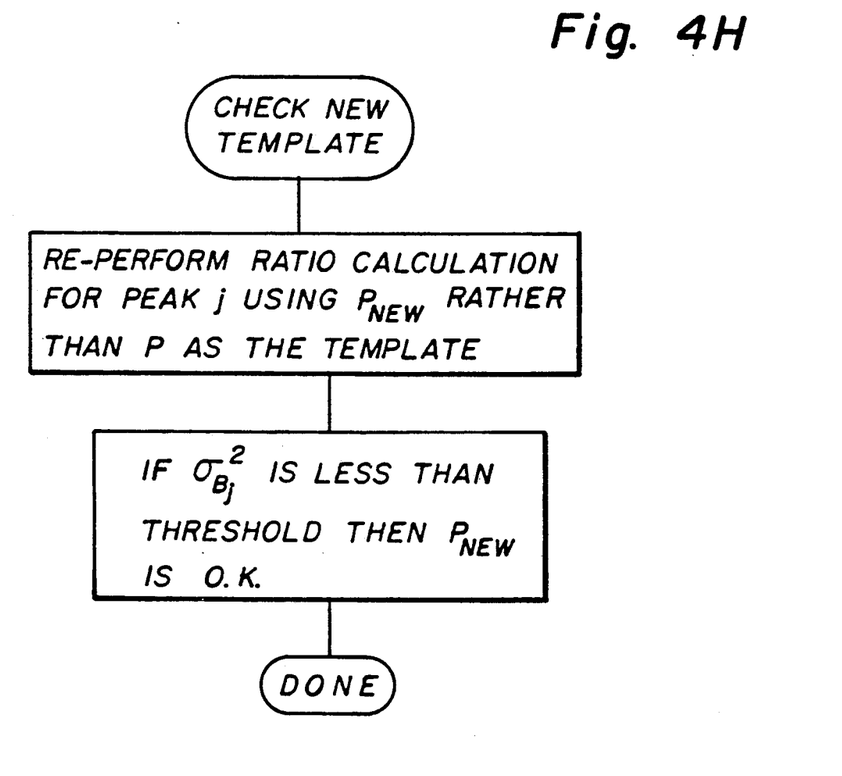

FIG. 4H shows the template checking procedure. The provisional template is used in place of the existing template to re-calculate the base ratio and ratio variance for the current peak. If the variance so calculated does not exceed a fixed threshold, then the provisional template shape is assumed to be good, and is used to update the actual template array.

EXAMPLE

The method described above was implemented using a Du Pont Genesis TM 2000 DNA Analysis System and an Apple MaCintosh TM II computer. Programming was done in the TrueBasic TM language [True Basic, Inc., 39 South Main Street, Hanover, NH 03755]. Flowcharts of this program are those shown in FIG. 4A–H.

The program differs from the above method in one respect. Accuracy was found to be enhanced when the linear regression analysis was done by fitting R' and T' to P' and P'', rather than by fitting R and T to P and P' as described above.

All of these samples were run using the standard protocols used with the Genesis TM 2000 DNA Analysis System.

Results of a comparison of the peak-template method to a non-template-based method are shown in Table 1. A clear advantage for the template method in run length at high (98%) accuracy can be seen.

TABLE 1

| Sample | Bases @ 98% | 4.0 b12/13 % ambiguous or uncallable | Bases @ 98% | 5.0 a1 % ambiguous or uncallable |
|---|---|---|---|---|
| M13 − 40 (MAJ) | 320 | 5.00 | 355 | 5.35 |
| M13 + 375 (MAJ) | 322 | 7.14 | 359 | 7.52 |
| M13 + ~500 (MAJ) | 332 | 5.12 | 411 | 4.14 |
| M13 + ~800 (MAJ) | 307 | 5.50 | 364 | 4.90 |
| M13 − 40 (WM) | 325 | 4.92 | 407 | 9.83 |
| M13 − 40 (WM) | 202 | 2.48 | 415 | 10.12 |
| M13 − 40 (WM) | 190 | 1.58 | 391 | 13.04 |
| M13 − 40 (WM) | 325 | 2.46 | 429 | 7.23 |
| PDP-1 | 320 | 1.56 | 367 | 9.26 |
| D.S (DAB819) | 226 | 3.10 | 320 | 9.06 |
| 296-Seq.3 (GT) | 60 | 5.00 | 60 | 6.67 |
| 296-Seq.1 (GT) | 319 | 3.76 | 335 | 5.97 |
| 296-Seq. (GT) | 321 | 5.61 | 334 | 6.59 |
| M13MP18 − 40 | 395 | 3.80 | 389 | 3.34 |
| M13MP18 − 40 | 362 | 2.49 | 378 | 5.29 |
| M13MP18 − 40 | 444 | 7.88 | 447 | 6.71 |
| M13MP18 − 40 | 265 | 5.66 | 297 | 6.73 |
| Average | 296.18 | 4.30 | 356.35 | 7.16 |
| S.D. | 87.95 | 1.85 | 86.25 | 2.46 |

What is claimed is:

1. In a method for obtaining signals characteristic of different species following the species separation in time and/or space and determining the identity of such species, the method including generating a first signal that varies in amplitude in a first sense to form peaks as a function of the nature of the species, generating a second signal that varies in amplitude in a second sense different than the first sense to form peaks as a function of the nature of the species, any peak of the first and second signal being approximately representable by the sum of three or more peak templates, and obtaining a third signal corresponding to the ratio of the first and second signals, the amplitude of the third signal being indicative of the identity of each of the species, the improvement wherein the third signal is obtained by the steps:

finding a sequence of peaks XYX in each of the first and second signals where X represents one species and Y represents another species, subtracting a fraction of the first signal from the second signal from approximately the peak center of the first X to approximately the peak center of the second X in each sequence of peaks to obtain differences such that the amplitude of the X peaks in each difference is substantially zero, thereby obtaining a prototypical template for a peak, and fitting the respective prototypical template to the respective first and second signals to obtain the peak amplitude of the first and second signals for obtaining the third signal from the ratio of such peak amplitudes.

2. The method set forth in claim 1 further characterized by:

differentiating the prototypical templates of the first and second signals one or more times, and fitting by least squares the sum of the prototypical templates for each signal and their corresponding derivatives to each first and second signals.

3. The method set forth in claim 1 further characterized by:

shifting the prototypical templates from each signal forward and backward with respect to the preceding and succeeding peak position in order to reduce the summed squared difference between each signal and a weighted sum of the templates.

4. The method set forth in claim 3 achieved by:

fitting each signal to a weighted sum of shifted prototypical templates and their derivatives, so that the derivatives terms minimize the summed squared differences between each signal and the corresponding summed templates by compensating for errors in the choices of initial prototypical template positions.

5. The method set forth in claim 4 further characterized by differentiating the prototypical and shifted templates of the first and second signal spectrums before the least squares fitting.

6. In a method for obtaining signals characteristic of different species following the species separation in time and/or space and determining the identity of such species, the method including generating a first signal that varies in amplitude in a first sense to form peaks as a function of the nature of the species, generating a second signal that varies in amplitude in a second sense different than the first sense to form peaks as a function of the nature of the species, any peak of the first and second signal being approximately representable by the sum of three successive peak templates, and obtaining a third signal corresponding to the ratio of the peaks in the first and second signal, the amplitude of the third signals being indicative of the identity of each of the species, the improvement wherein the third signal is obtained by the steps:

obtaining a template for fitting to each of the signals, and fitting the templates to the respective first and second signals to obtain the peak amplitude of the first and second signals for obtaining the third signal from the ratio of such peak amplitudes.

7. The method set forth in claim 6 further characterized by:

differentiating the template for fitting the first and second signals, and fitting by least squares the sum of the templates and their derivatives to each first and second signals.

8. The method of claim 7 further characterized by finding the combination of templates and their derivatives that fit each of the first and second signals, thereby to determine the first and second signal amplitudes for each peak.

* * * * *